Aug. 29, 1961 R. L. BYRUM Plant Pat. 2,084
ROSE PLANT
Filed Nov. 3, 1960
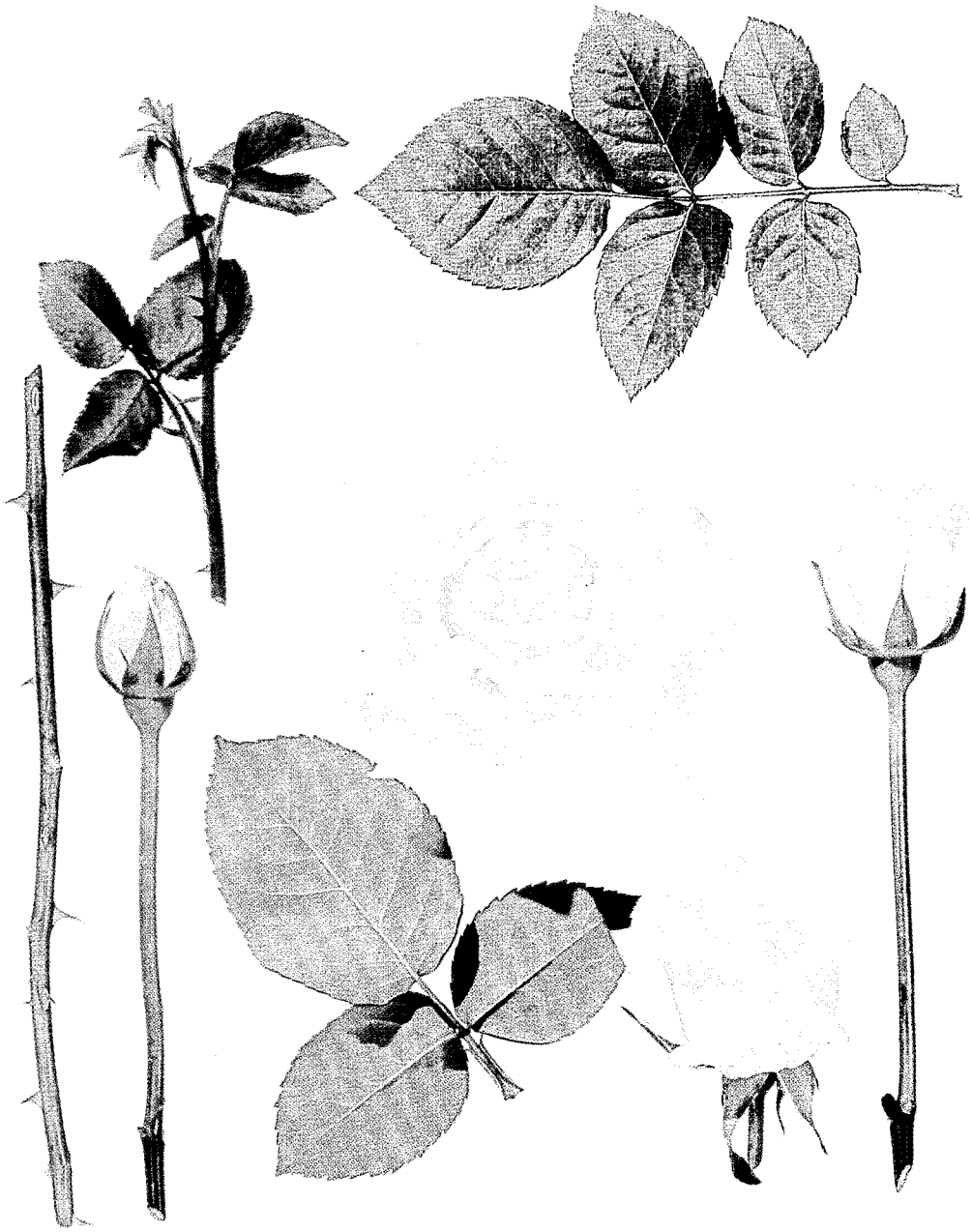
INVENTOR
R. L. Byrum
BY Robb & Robb
ATTORNEYS United States Patent Office Plant Pat. 2,084
Patented Aug. 29, 1961

2,084
ROSE PLANT

Roy L. Byrum, Richmond, Ind., assignor to Joseph H. Hill Company, Richmond, Ind., a corporation of Indiana Filed Nov. 3, 1960, Ser. No. 67,142
1 Claim. (Cl. 47—61)

The present invention relates to a new and distinct variety of rose plant of the hybrid tea class, which was originated by me by crossing the variety "Mary Jo" (Plant Patent No. 1,504) with the variety "Lamplighter" (Plant Patent No 1,804).

The primary objective of this breeding was to produce a new rose variety having improved color characteristics as compared with both parent varieties, while retaining the productivity of the seed parent, "Mary Jo," as well as improved disease resistance. This objective was fully achieved along with other desirable improvements, as evidenced by the following characteristics which are outstanding in the new variety and distinguish it from its parents, as well as from all other varieties of which I am aware:

(1) A clean and upright growing habit;
(2) Good foliage and good resistance thereof to mildew;
(3) Good flower productivity;
(4) Strong, sturdy and exceptionally straight stems;
(5) Good form of the open flowers;
(6) Large flower size;
(7) Heavy textured petals; and
(8) A uniform and distinctive Aureolin general color tonality of the flowers which does not change under adverse weather conditions.

In comparison with its seed parent, "Mary Jo," the new variety is a more upright grower; has better foliage; has sturdier and stronger stems; bears larger flowers, and the color of the flowers does not change under adverse weather conditions.

As compared with its pollen parent, "Lamplighter," the flowers of my new variety have better form when open; the flower petals are heavier textured and the flowers are more uniform in color the year round.

Asexual reproduction of my new variety by both budding and grafting, as performed at Richmond, Indiana, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticulture Colour Chart (hereinafter abbreviated as "Wilson"), and Koster's Color Guide (hereinafter abbreviated as "Koster"), except where general color terms of ordinary dictionary significance are obvious:

Type: Bush; seedling.
Class: Hybrid tea.
Breeding: Seedling.
*Seed parent.*—"Mary Jo."
*Pollen parent.*—"Lamplighter."
Propagation: Holds its distinguishing characteristics through succeeding propagations by both grafting and budding.

*Flower*

Locality where grown and observed: Richmond, Indiana.

Flowers borne: Singly to stem; on strong stems of medium length.
Quantity of bloom: Abundant, in greenhouse.
Continuity: Continuous.
Fragrance: Penetrating. Nature—tea.
Bud:
*Peduncle.*—Medium length; medium diameter; strong; erect. Bark—almost smooth. Color—Scheeles Green, Plate 860 (Wilson). Thorns—none. Prickles—few; color—Pure White, Plate 1 (Koster), with base Rose Pink, Plate 427/3 (Wilson). Hairs—none.
*Before calyx breaks.*—Size—medium large. Form—ovoid; with a conspecious neck; with foliaceous appendages on the surface of the bud; with slender foliaceous parts extending beyond the tip of the bud equal to ¼ or more of its length. Color—Sap Green, Plate 62/2 (Wilson).
*As calyx breaks.*—Color (outside of petal)—Empire Yellow, Plate 603 (Wilson).
*As first petal opens.*—Size—large. Form—ovoid. Color: outside—base of petal Aureolin, Plate 3/1 (Wilson), gradually changing to Aureolin, Plate 3/2 (Wilson) at top of petal; inside—base of petal Lemon Yellow, Plate 4 (Wilson), gradually changing through Lemon Yellow, Plate 4/1 (Wilson) to Lemon Yellow, Plate 4/2 (Wilson) at top of petal; some petals have light streak starting at base and gradually diminishing at top of petal.
*Opening.*—Opens up well in greenhouse; no unusual characteristics attributed to weather conditions.
Bloom:
*Size (when fully open).*—Large; from 4 inches to 5 inches. *Petalage.*—Double (more petals but the stamens not hidden); from 55 to 60 petals; arranged irregularly.
*Form.*—Full, high-centered and globular at first, but becoming open; petals being at first very tightly rolled outward, but later becoming loosely rolled outward at maturity.
Petals:
*Texture.*—Moderately thick; leathery. Inside—satiny. Outside—shiny.
*Shape.*—Outer petals—obovate, with apex obtuse. Intermediate petals—obovate, with apex obtuse. Inner petals—obovate, with apex retuse and some with from 1 to 3 notches.

This description of a newly opened flower was made from a rose grown in a greenhouse during the month of June at Richmond, Indiana:

*Color.*—Outer petal: outside surface—Empire Yellow, Plate 603/1 (Wilson) at base, gradually changing to Empire Yellow, Plate 603/2 (Wilson) at top of petal; inside surface—base of petal Aureolin, Plate 3 (Wilson), gradually changing through Aureolin, Plate 3/1 (Wilson) to Aureolin, Plate 3/2 (Wilson) at the top of petal. Intermediate petal: Outside surface—Aureolin, Plate 3/1 (Wilson) at base, gradually changing to Aureolin, Plate 3/2 (Wilson) at top of petal; inside surface—Aureolin, Plate 3 (Wilson) at base of petal, gradually changing through Aureolin, Plate 3/1 (Wilson) to Aureolin, Plate 3/2 (Wilson) at top of petal. Inner petal: outside surface—Lemon Yellow, Plate 4/1 (Wilson) at base of petal, gradually changing to Lemon Yellow, Plate 4/2 (Wilson) at top of petal; inside surface—Lemon Yellow, Plate 4 (Wilson) at base of petal, gradually changing to Lemon Yellow, Plate 4/1 (Wilson) at top of petal.

This description was made from a rose that was open for three days in a greenhouse during the month of July at Richmond, Indiana:

*Color.*—Outer petal: outside surface—Empire Yellow, Plate 603/1 (Wilson) at base, gradually changing through Empire Yellow, Plate 603/2 (Wilson) and through Empire Yellow, Plate 603/3 (Wilson) to Primrose Yellow, Plate 601/3 (Wilson) at top of petal; inside surface—Empire Yellow, Plate 603 (Wilson) at base of petal, gradually changing through Empire Yellow, Plate 603/1 (Wilson) to Empire Yellow, Plate 603/2 (Wilson) at top of petal. Intermediate petal: outside surface—Empire Yellow, Plate 603 (Wilson) at base of petal, gradually changing through Empire Yellow, Plate 603/1 (Wilson) to Empire Yellow, Plate 603/2 (Wilson) at top of petal; inside surface—Empire Yellow, Plate 603 (Wilson) at base of petal, gradually changing through Empire Yellow, Plate 603/1 (Wilson) to Empire Yellow, Plate 603/2 (Wilson) at top of petal. Inner petal: outside surface—Empire Yellow, Plate 603 (Wilson) at base of petal, gradually changing through Empire Yellow, Plate 603/1 (Wilson) to Empire Yellow, Plate 603/2 (Wilson) at top of petal; inside surface—Empire Yellow, Plate 603 (Wilson) at base of petal, gradually changing to Empire Yellow, Plate 603/1 (Wilson) at top of petal.

*General color effect.*—Newly opened flower—Aureolin, Plate 3/2 (Wilson). Three days open—Aureolin, Plate 3/2 (Wilson).

*Behavior.*—Persist in greenhouse; no unusual characteristics attributed to weather conditions; does not change color.

*Flower longevity.*—Cut roses grown in greenhouse and kept at livingroom temperatures—5 or 6 days in November, December, and July.

*Reproductive organs*

Stamens: Many; arranged irregularly about pistils.

Filaments: Medium length; most with anthers. Color—Orpiment Orange, Plate 10/2 (Wilson) at bottom, changing through Orpiment Orange, Plate 10/3 (Wilson) to Chinese Yellow, Plate 606/2 (Wilson) at top.

Anthers: Medium large; all open at once. Color—Empire Yellow, Plate 603/1 (Wilson).

Pollen: Sparse. Color—Naples Yellow, Plate 403/3 (Wilson).

Pistils: Many.

Styles: Uneven; medium length; medium heavy; bunched. Color—Naples Yellow, Plate 403/3 (Wilson).

Stigma: Color—Rose Madder, Plate 23 (Wilson).

Ovularies: Most all enclosed in calyx.

Hips: None observed.

Sepals: Permanent; medium length; straight. Color: inside—Scheeles Green, Plate 860/2 (Wilson), overlaid with white fuzz; outside—Scheeles Green, Plate 860 (Wilson).

Seeds: Few; medium large.

*Plant*

Foliage:

*Leaves.*—Compound of 3–5 leaflets; abundant; large size; heavy.

*Leaflets.* — Shape — ovoid. Apex — acuminate. Base—round. Margin—simply serrate.

*Color.*—Mature: upper surface—slightly darker than Spinach Green, Plate 0960 (Wilson); under surface—slightly lighter than Cedar Green, Plate 80 (Koster). Young: upper surface—Lettuce Green, Plate 861/3 (Wilson), irregularly overlaid with Dark Violet, Plate 58 (Koster); under surface—Fern Green, Plate 0862/3 (Wilson), irregularly overlaid with Violet, Plate 59 (Koster).

*Rachis (the supporting stem of the compound leaf).*—Heavy. Upper side—smooth; grooved. Under side—moderately thorny.

*Stipules.*—Medium length; medium width; with short points turning out at an angle of more than 45°.

Growth:

*Habit.*—Bush; upright; much-branched.

*Growth.*—Free; vigorous.

*Canes.*—Large diameter.

*Main stems.*—Color—Spinach Green, Plate 0960 (Wilson), overlaid with Maroon, Plate 97 (Koster) in irregular blotches and stripes. Thorns—several; medium length; hooked downward; with long, narrow base; color—Bistre, Plate 93 (Koster). Prickles—none. Hairs—none.

*Branches.*—Color—varies from Scheeles Green, Plate 860 (Wilson) through Scheeles Green, Plate 860/1 (Wilson) to Scheeles Green, Plate 860/2 (Wilson). Thorns — several; medium length; hooked downward; with long, narrow base; color—Deep Carmine Violet, Plate 46 (Koster), with Pod Green, Plate 061/2 (Wilson) at tip. Prickles—none. Hairs—none.

*New shoots.*—Color—near Oxblood Red, Plate 00823/3 (Wilson). Thorns—several; medium length; mostly straight; with long, narrow base; color—near Oxblood Red, Plate 00823/3 (Wilson), with Chartreuse Green, Plate 663/3 (Wilson) at tip. Prickles—none. Hairs—none.

I claim:

A new and distinct variety of rose plant of the hybrid tea class, substantially as herein shown and described, characterized particularly as to novelty by the unique combination of a clean and upright growing habit, good foliage and good resistance thereof to mildew, good flower productivity, strong, sturdy and exceptionally straight stems, good form of the open flowers, large flower size, heavy textured petals, and a uniform and distinctive Aureolin general color tonality of the flowers which does not change under adverse weather conditions.

No references cited.